(12) United States Patent
Koyrakh et al.

(10) Patent No.: US 9,125,573 B2
(45) Date of Patent: Sep. 8, 2015

(54) ELECTRICALLY TRANSPARENT INTRODUCER SHEATH

(75) Inventors: Lev A. Koyrakh, Plymouth, MN (US); Daniel J. Potter, Stillwater, MN (US); Jeffrey A. Schweitzer, St. Paul, MN (US); D. Curtis Deno, Andover, MN (US); Anthony D. Hill, Minneapolis, MN (US); Dale Eric Just, Minneapolis, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 735 days.

(21) Appl. No.: 13/339,547

(22) Filed: Dec. 29, 2011

(65) Prior Publication Data

US 2013/0172712 A1 Jul. 4, 2013

(51) Int. Cl.
*A61B 5/04* (2006.01)
*A61M 25/06* (2006.01)
*A61B 5/053* (2006.01)
*A61B 5/145* (2006.01)
(Continued)

(52) U.S. Cl.
CPC .................. *A61B 5/04* (2013.01); *A61B 5/0538* (2013.01); *A61B 5/14503* (2013.01); *A61M 25/0662* (2013.01); *A61B 5/02444* (2013.01); *A61B 2560/06* (2013.01); *A61M 25/005* (2013.01)

(58) Field of Classification Search
CPC ...... A61B 1/00154; A61B 5/04; A61B 5/042; A61B 5/0538; A61B 5/4887–5/4896; A61B 2018/00071; A61M 25/0662; A61M 2025/0681

USPC ...................... 600/373–381; 606/32–35, 129; 607/115–156
See application file for complete search history.

(56) References Cited

U.S. PATENT DOCUMENTS

| 4,623,329 A | 11/1986 | Drobish et al. |
| 4,800,898 A | 1/1989 | Hess |

(Continued)

FOREIGN PATENT DOCUMENTS

| EP | 0677301 | 10/1995 |
| EP | 1935448 | 6/2008 |

(Continued)

OTHER PUBLICATIONS

"PCT Search Report & Written Opinion", PCT/US2012/026979 Jun 29, 2012.

(Continued)

*Primary Examiner* — Linda Dvorak
*Assistant Examiner* — Erin M Cardinal
(74) *Attorney, Agent, or Firm* — Dykema Gossett PLLC

(57) ABSTRACT

An introducer sheath for a medical device is provided. The sheath includes a deformable, elongate body disposed about a longitudinal axis. The body has proximal and distal ends and defines a lumen extending between the proximal and distal ends and configured to allow passage of the medical device therethrough. The body is configured to allow an electric current to pass radially between a space outside of the body and the lumen such that the position of the medical device within a patient can be monitored and electrogram readings from body tissues can be measured while the device is in the sheath. In some embodiments of the invention, the body may include a one or more apertures extending from the radially outer surface of the body to the lumen or a portion of the body may be made from a conductive and/or fluid permeable material.

19 Claims, 15 Drawing Sheets

(51) Int. Cl.
    *A61B 5/024*        (2006.01)
    *A61M 25/00*        (2006.01)

(56) References Cited

U.S. PATENT DOCUMENTS

| | | | |
|---|---|---|---|
| 5,080,660 A * | 1/1992 | Buelna | 606/45 |
| 5,429,130 A * | 7/1995 | Goldman | 600/374 |
| 5,573,520 A * | 11/1996 | Schwartz et al. | 604/526 |
| 5,651,767 A | 7/1997 | Schulman et al. | |
| 5,785,706 A * | 7/1998 | Bednarek | 606/41 |
| 5,824,030 A | 10/1998 | Yang et al. | |
| 5,919,188 A * | 7/1999 | Shearon et al. | 606/41 |
| 5,925,041 A * | 7/1999 | Long et al. | 606/41 |
| 5,993,462 A * | 11/1999 | Pomeranz et al. | 606/129 |
| 6,010,500 A * | 1/2000 | Sherman et al. | 606/41 |
| 6,332,880 B1 | 12/2001 | Yang et al. | |
| 7,248,913 B2 | 7/2007 | Hassett | |
| 7,263,397 B2 | 8/2007 | Hauck et al. | |
| 7,603,179 B1 | 10/2009 | Grandhe | |
| 7,914,515 B2 | 3/2011 | Heideman et al. | |
| 8,340,783 B2 * | 12/2012 | Sommer et al. | 607/116 |
| 8,597,193 B2 * | 12/2013 | Grunwald et al. | 600/468 |
| 2002/0183817 A1 * | 12/2002 | Van Venrooij et al. | 607/116 |
| 2003/0208195 A1 | 11/2003 | Thompson et al. | |
| 2003/0233091 A1 | 12/2003 | Whayne | |
| 2007/0299424 A1 | 12/2007 | Cumming et al. | |
| 2008/0071221 A1 | 3/2008 | Rickerd | |
| 2008/0132970 A1 * | 6/2008 | Barolat | 607/46 |
| 2010/0121345 A1 | 5/2010 | Brasington et al. | |
| 2010/0160862 A1 | 6/2010 | Howat et al. | |
| 2010/0174170 A1 * | 7/2010 | Razavi | 600/371 |
| 2010/0217257 A1 | 8/2010 | Howat et al. | |
| 2011/0077598 A1 | 3/2011 | Pipenhagen et al. | |

FOREIGN PATENT DOCUMENTS

| | | |
|---|---|---|
| EP | 0916360 | 11/2010 |
| WO | 03/084398 | 10/2003 |

OTHER PUBLICATIONS

Supplementary European Search Report in EP Application No. 12861474.0 (Mar. 16, 2015).

* cited by examiner

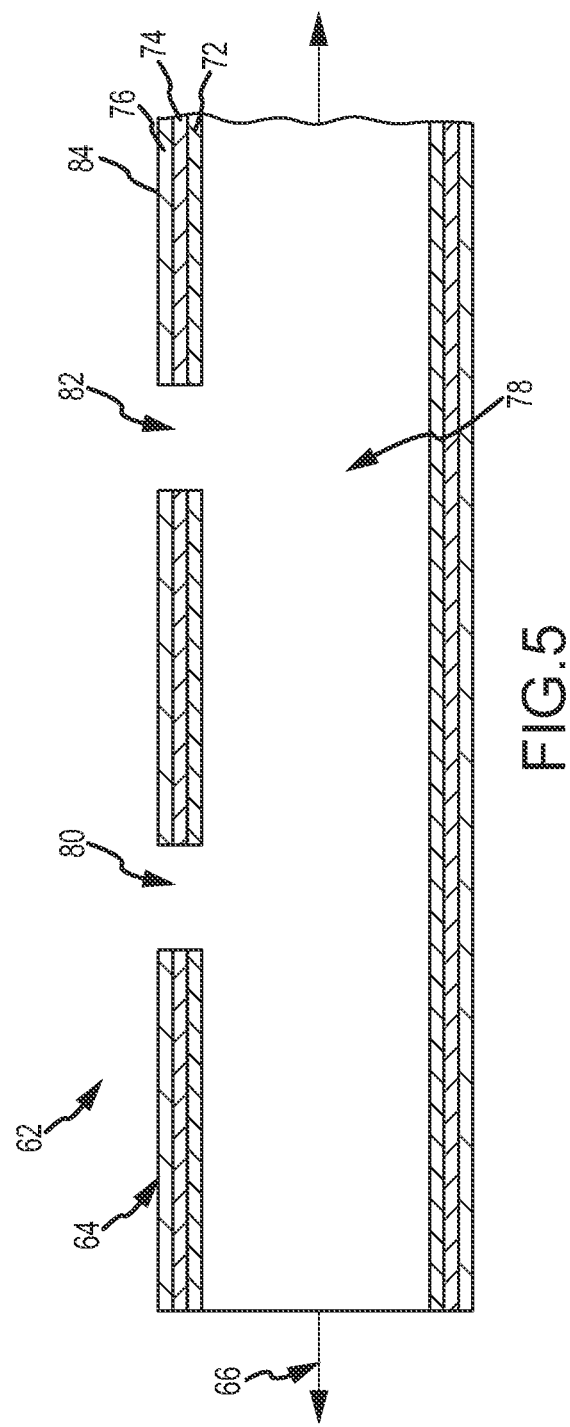

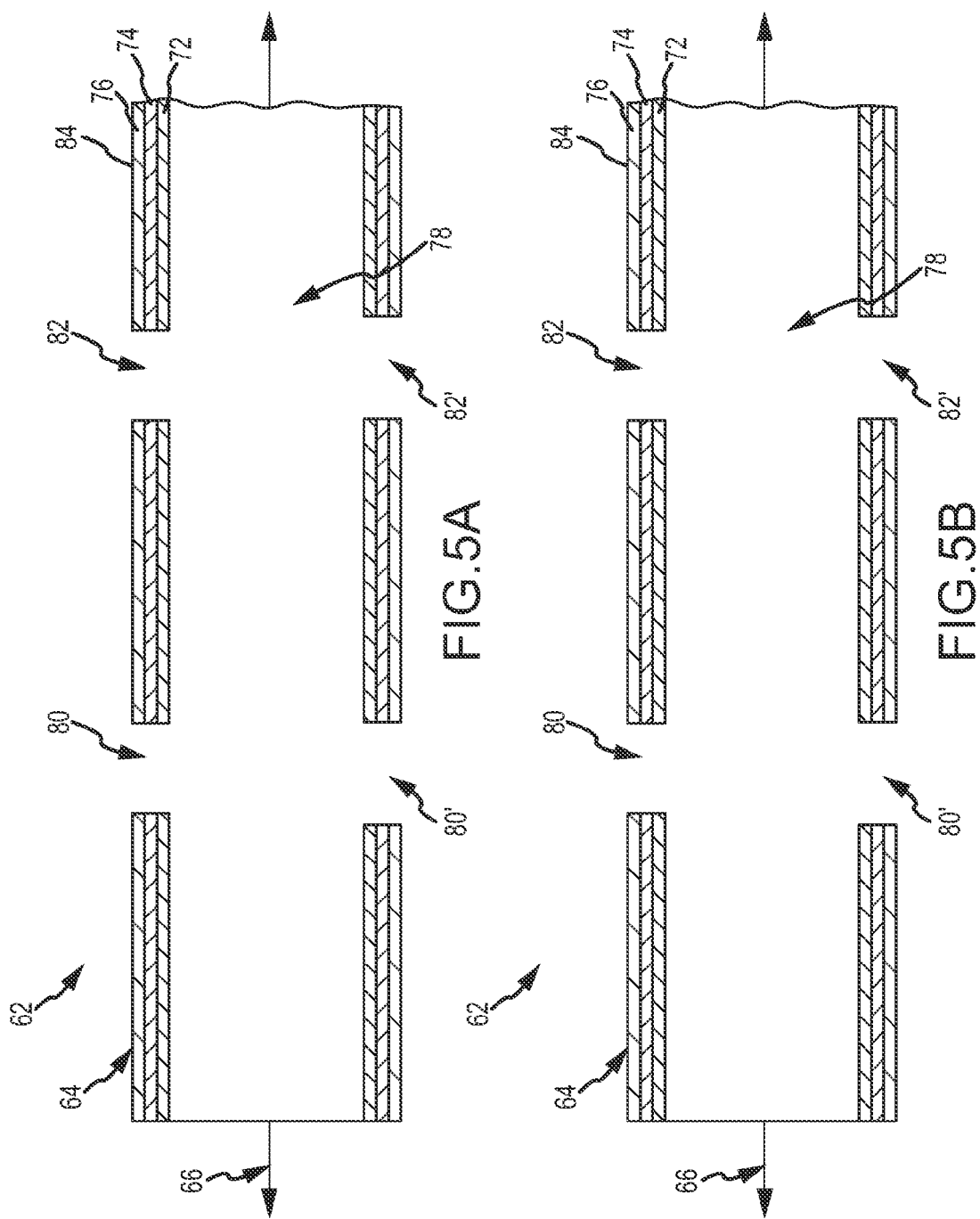

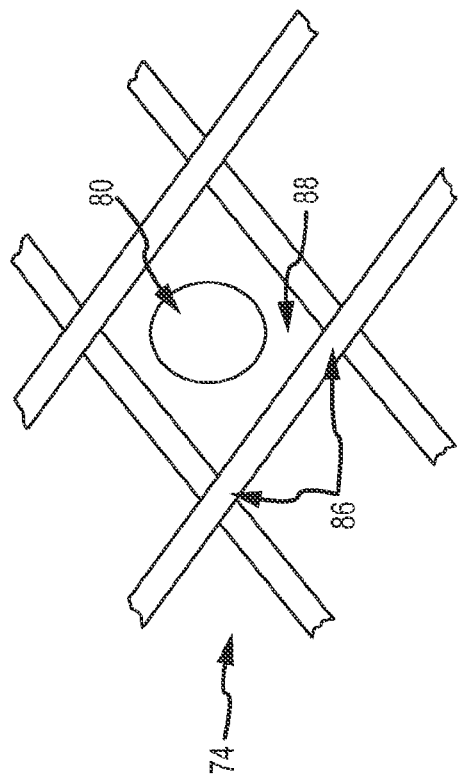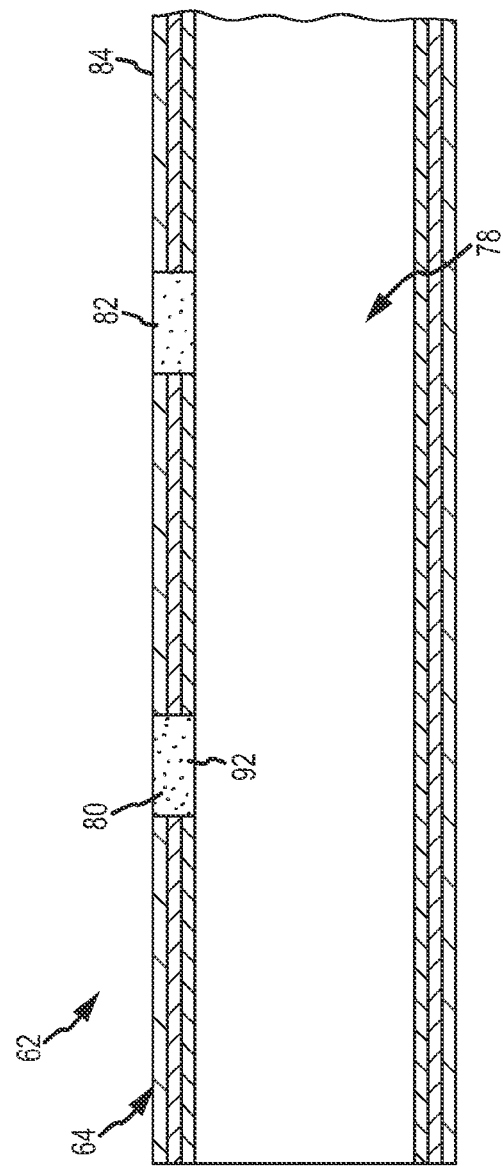

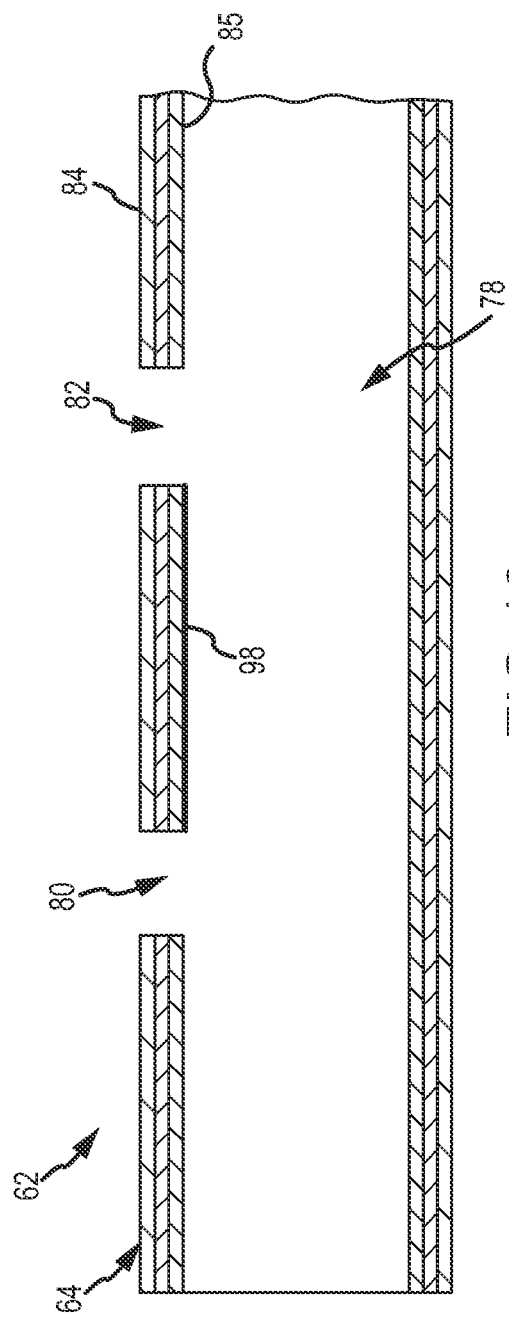
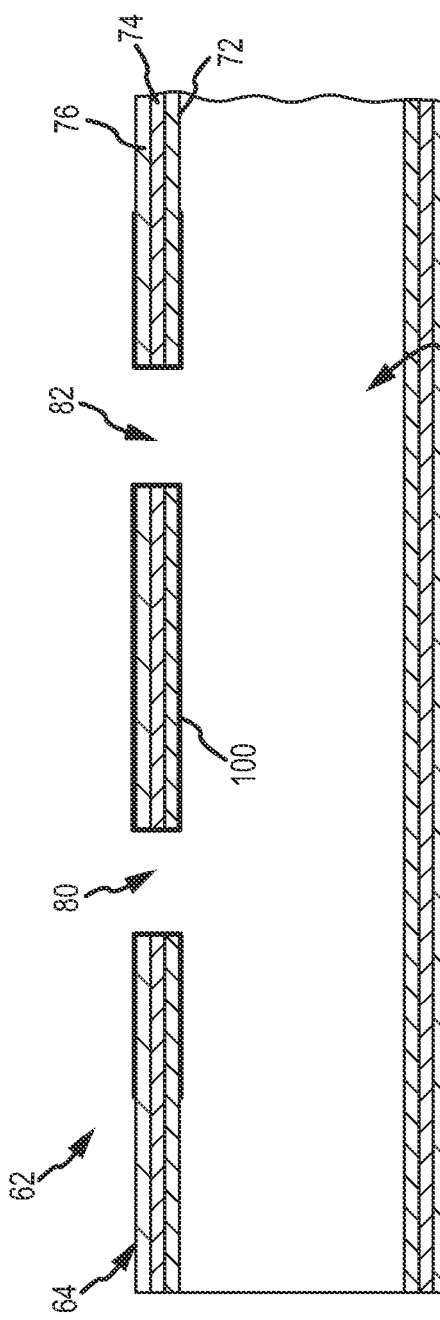

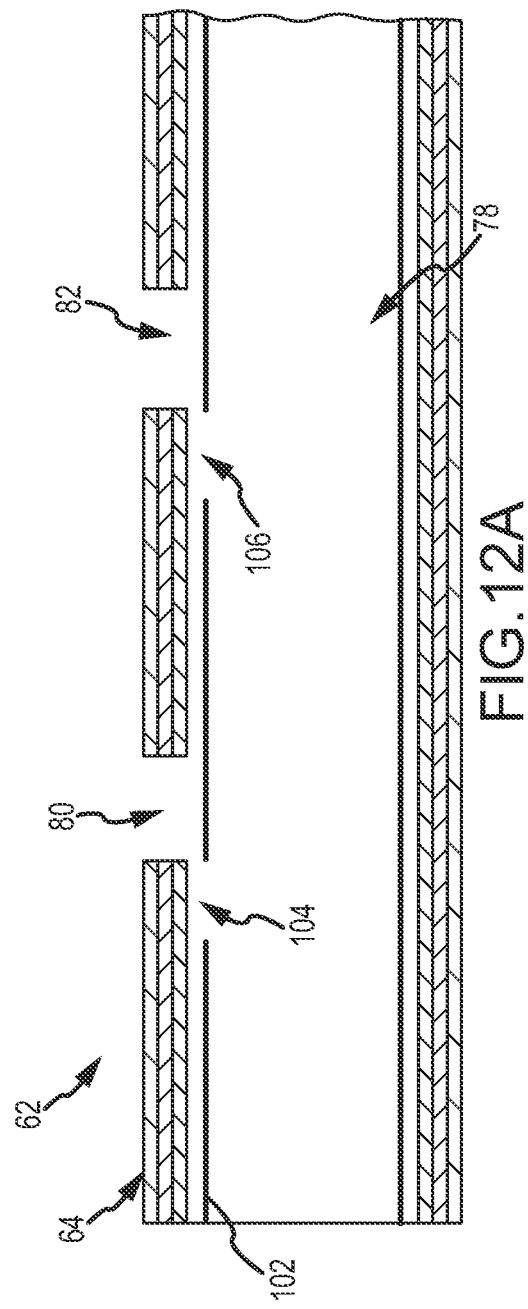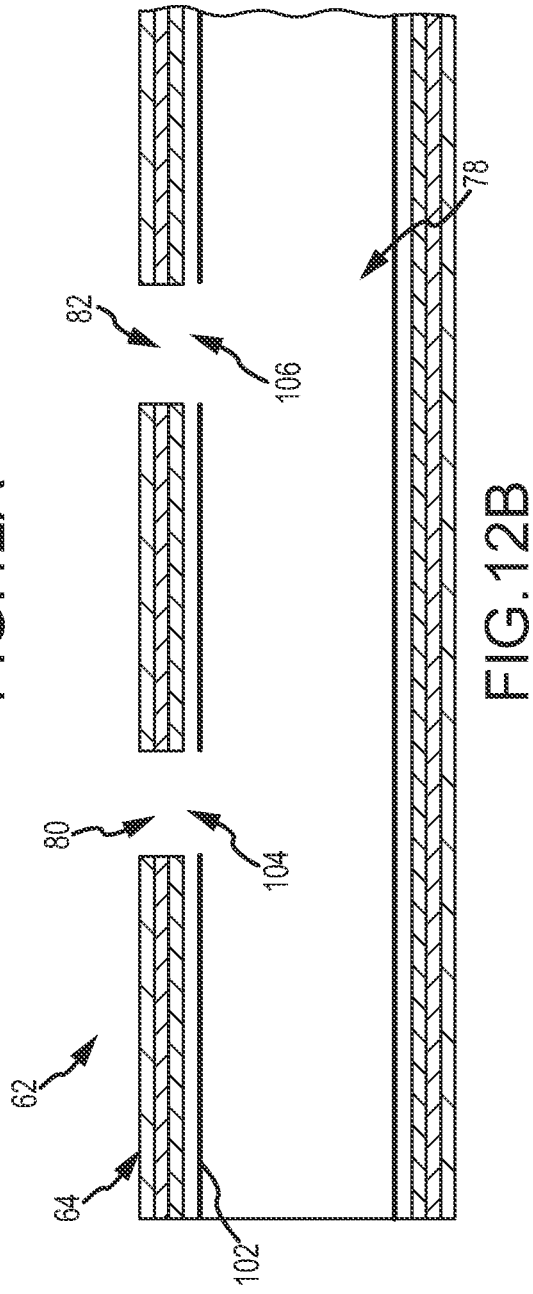

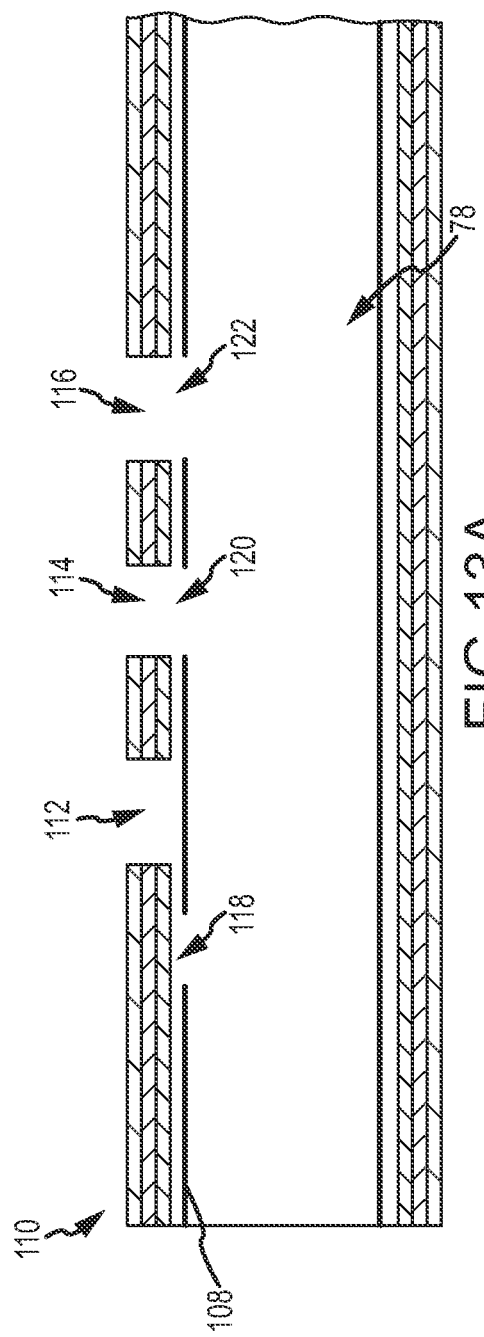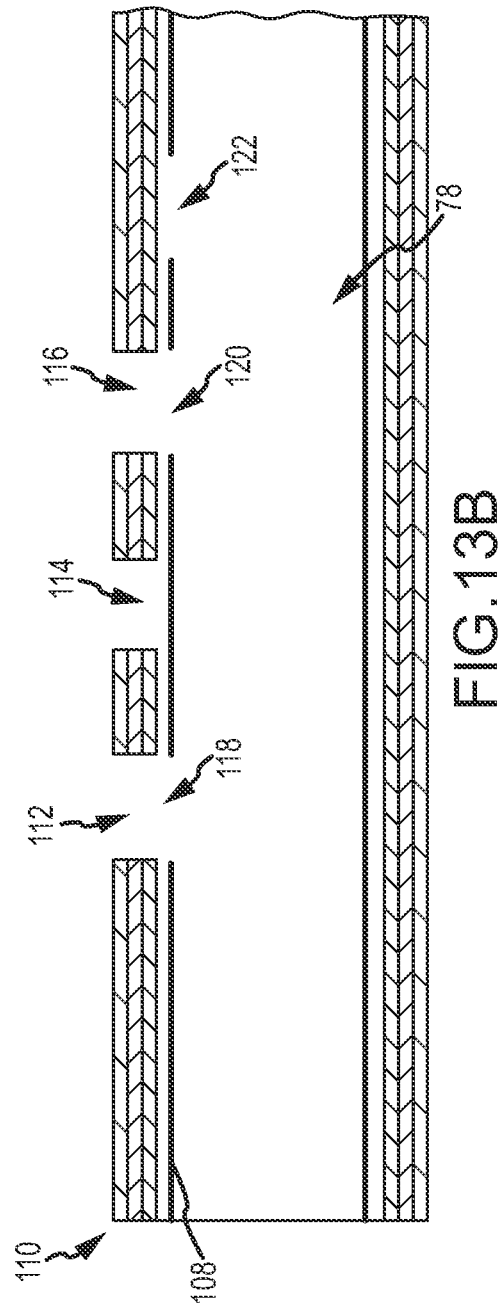

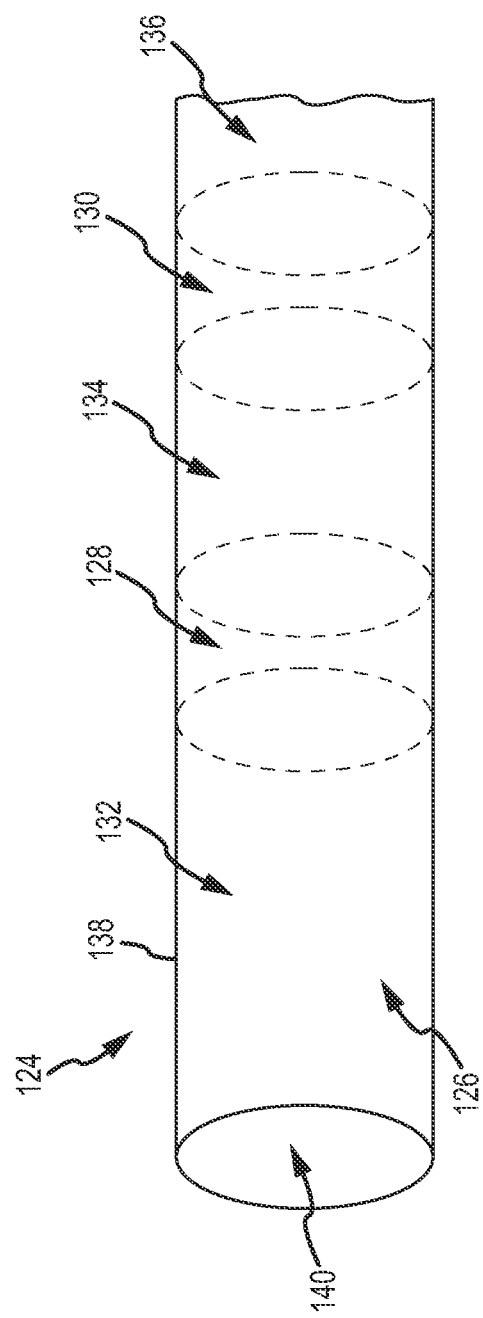

ELECTRICALLY TRANSPARENT INTRODUCER SHEATH

BACKGROUND OF THE INVENTION a. Field of the Invention

This invention relates to introducers for inserting and guiding medical devices within a body. In particular, the instant invention relates to an introducer sheath configured to allow electric currents generated by body electrical activity or sources external to the body to pass through the sheath and/or to a medical device contained therein.

b. Background Art

A wide variety of medical devices are inserted into the body to diagnose and treat various medical conditions. Catheters, for example, are used to perform a variety of tasks within human bodies and other bodies including the delivery of medicine and fluids, the removal of bodily fluids and the transport of surgical tools and instruments. In the diagnosis and treatment of atrial fibrillation, for example, catheters may be used to deliver electrodes to the heart for electrophysiological mapping of the surface of the heart and to deliver ablative energy to the surface among other tasks. Catheters are typically routed to a region of interest through the body's vascular system. In a conventional approach, an introducer is used to puncture the skin surface and a sheath having an inner diameter greater than the outer diameter of the catheter is threaded through the vasculature to a region of interest. The catheter is then moved longitudinally through the sheath to the region of interest either manually by a clinician or through the use of electromechanical drive systems.

Conventional introducer sheaths are constructed from electrically insulating materials which prevent electric currents from penetrating the sheath and reaching the catheter. As a result, it is not possible for electrodes on the catheter to measure electrical activity (i.e. electrograms) from surrounding tissues while in the sheath even though this information may be relevant to diagnosis or treatment. Medical device positioning systems may also rely on signals generated by catheter electrodes in response to externally generated electric fields to determine the position of the catheter and guide the catheter to a target location. Because conventional sheaths prevent electric currents from reaching the electrodes, the position of the catheter electrodes within the sheath cannot be directly monitored and incorrect position information may be generated. This deficiency is especially problematic when the catheter is used as a positional reference for other catheters and measurements.

The inventors herein have recognized a need for an introducer sheath that will minimize and/or eliminate one or more of the above-identified deficiencies. The foregoing discussion is intended only to illustrate the present field and should not be taken as a disavowal of claim scope.

BRIEF SUMMARY OF THE INVENTION

In various embodiments, it is desirable to provide an introducer sheath for a medical device that is configured to allow external electric currents generated by body electrical activity or sources external to the body to pass through the sheath to a medical device contained therein.

An introducer sheath for a medical device in accordance with the present invention includes a deformable, elongate body disposed about a longitudinal axis. The body has proximal and distal ends and defines a lumen extending between the proximal and distal ends and configured to allow passage of the medical device therethrough. The body is configured to allow an electric current to pass radially between a space outside the body and the lumen. In one embodiment of the invention, the body includes one or more apertures that extend from the radially outer surface of the body to the lumen. In certain embodiments, electrically conductive materials may be disposed within the apertures. In another embodiment, one or more longitudinal sections of the body are made from an electrically conductive material.

An introducer sheath for a medical device in accordance with another embodiment of the present invention includes an elongate body disposed about a longitudinal axis. The body has proximal and distal ends and defines a lumen extending between the proximal and distal ends and configured to allow passage of the medical device therethrough. The sheath further includes means for allowing an electric current to pass radially between a space outside the body and the lumen.

An introducer sheath in accordance with the present invention is advantageous relative to conventional introducer sheaths because the inventive sheath permits the passage of external electric currents generated by body electrical activity or sources originating external to the body to reach the medical device contained in the sheath. As a result, the device can monitor electrical activity of surrounding tissues while in the sheath. The device can also be tracked and guided using medical positioning systems employing electric fields.

The foregoing and other aspects, features, details, utilities and advantages of the present invention will be apparent from reading the following description and claims, and from reviewing the accompanying drawings.

BRIEF DESCRIPTION OF THE DRAWINGS

Various features of the embodiments described herein are set forth with particularity in the appended claims. The various embodiments, however, both as to organization and methods of operation, together with advantages thereof, may be understood in accordance with the following description taken in conjunction with the accompanying drawings as follows.

FIG. 5 is a cross-sectional view of the introducer sheath of FIG. 4 taken along lines 5-5.

FIG. 5A is a cross-sectional view of an introducer sheath in accordance with another embodiment of the present invention.

FIG. 5B is a cross-sectional view of an introducer sheath in accordance with another embodiment of the present invention.

FIG. 6 is a diagrammatic view of a portion of an introducer sheath in accordance with one embodiment of the invention.

FIG. 7 is a cross-sectional view of an introducer sheath in accordance with another embodiment of the present invention.

FIG. 10 is a cross-sectional view of an introducer sheath in accordance with another embodiment of the present invention.

FIG. 11 is a cross-sectional view of an introducer sheath in accordance with another embodiment of the present invention.

FIGS. 12A-B are cross-sectional views of an introducer sheath in accordance with another embodiment of the present invention.

FIGS. 13A-B are cross-sectional views of an introducer sheath in accordance with another embodiment of the present invention.

FIG. 14 is a plan view of an introducer sheath in accordance with another embodiment of the present invention.

Corresponding reference characters indicate corresponding parts throughout the several views. The exemplifications set out herein illustrate various embodiments, in one or more forms, and such exemplifications are not to be construed as limiting the scope of the claims in any manner.

DETAILED DESCRIPTION OF EMBODIMENTS OF THE INVENTION

Various embodiments are directed to apparatuses, systems, and methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation provided that such combination is not illogical or non-functional.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Figure 1:
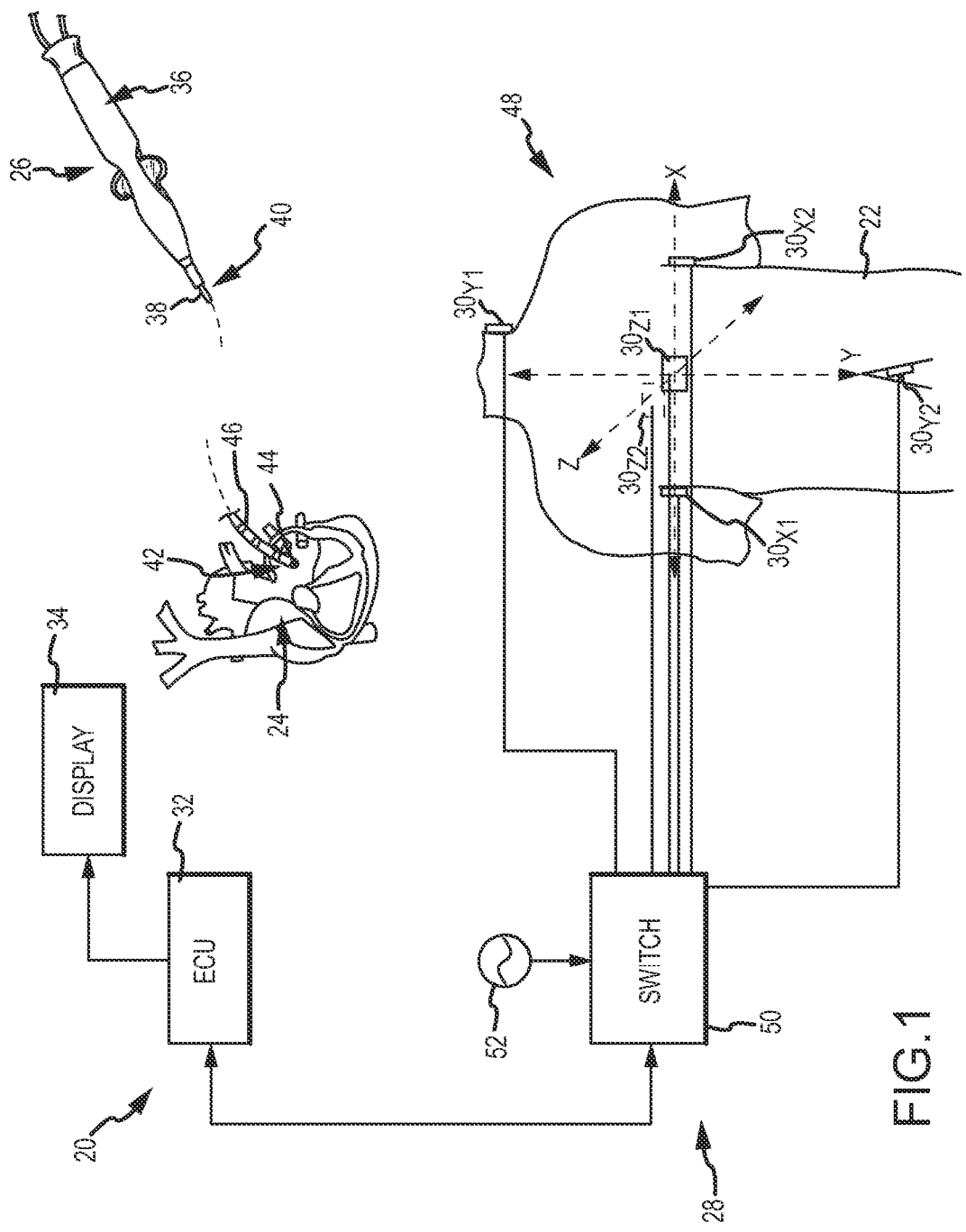
FIG. 1 is a diagrammatic view of a conventional system for diagnosis and treatment of cardiac tissues.

Referring now to the drawings wherein like reference numerals are used to identify identical or similar components in the various views, FIG. 1 illustrates a system 20 for diagnosis and/or treatment of tissues in a body 22, such as cardiac tissues in heart 24. Although the illustrated system relates to diagnosis and treatment of cardiac tissues, it should be understood that the present invention may find application in the diagnosis and treatment of a variety of tissues. System 20 includes a medical device 26 and a system 28 for determining the position of the medical device 26 including a plurality of patch electrodes 30 applied to body 22, an electronic control unit (ECU) 32 and a display 34.

Medical device 26 may comprise a deformable catheter of the type used to allow removal of bodily fluids or injection of fluids and medicine into body 22 and/or for transporting surgical tools or instruments within body 22 including those use for pacing or tissue ablation of heart 24. The catheter may be manipulated manually by a clinician or automatically through, for example, robotic controls and may be inserted within a vessel located near the surface of a body (e.g., in an artery or vein in the leg, neck, or arm) in a conventional manner and maneuvered to a region of interest in body 22 such as heart 24 under the guidance of system 28. Device 26 may, for example, comprise an electrophysiology (EP) mapping catheter for use in gathering EP data associated with heart 24 to enable generation of an image of the geometry of the heart surface and related EP data. Device 26 may alternatively comprise an intracardiac echocardiography (ICE) catheter used to generate an image of a region of interest within body 22 such as heart 24. Device 26 may alternatively comprise an ablation catheter used to ablate tissue within heart 24 to treat abnormal heart rhythms such as atrial fibrillation, ventricular tachycardia and similar conditions. Although examples of specific medical devices 26 associated with diagnosis and treatment of conditions associated with heart 24 have been described, it should be understood that the inventive system 22 may find application in connection with determining the position of a variety of medical devices in varying locations within human and non-human bodies. Medical device 26 may include a handle 36 and a tubular, deformable shaft 38 having a proximal end 40 and a distal 42 end (as used herein, "proximal" refers to a direction toward the end of the catheter near the clinician, and "distal" refers to a direction away from the clinician and (generally) inside the body of a patient) and one or more diagnostic or treatment elements, such as electrodes 44, supported thereon. Device 26 may also include other conventional components not illustrated herein such as a temperature sensor, additional electrodes, and corresponding conductors or leads. Device 26 also includes one or more position sensors 46. In the illustrated embodiment, positions sensors 46 are electrodes configured to generate an induced voltage responsive to the transmission of current by patch electrodes 30.

Patch electrodes 30 are provided to generate electrical signals used in determining the position of device 26 within a three dimensional coordinate system 48 of system 28. Electrodes 30 may also be used to measure EP data regarding heart 24. Electrodes 30 are placed on the surface of body 22 and are used to create axes specific electric fields within body 22. Electrodes $30_{X1}$, $30_{X2}$ may be placed along a first (x) axis. Similarly, electrodes $30_{Y1}$, $30_{Y2}$ may be placed along a second (y) axis and electrodes $30_{Z1}$, $30_{Z2}$ may be placed along a third (z) axis. Each of the electrodes 30 may be coupled to a multiplex switch 50. ECU 32 is configured through appropriate software to provide control signals to switch 50 and thereby sequentially couple pairs of electrodes 30 to a signal generator 52. Excitation of each pair of electrodes 30 generates an electromagnetic field within body 22 and within an area of interest such as heart 24. Voltage levels at non-excited electrodes 30 may be filtered and converted and provided to ECU 32 for use as reference values.

Electronic control unit (ECU) 32 provides a means for controlling the operation of various components of system 20 including device 26, display 34 and switch 50. ECU 32 also provides a means for determining the position and orientation of medical device 26. ECU 32 may comprise a programmable microprocessor or microcontroller or may comprise an application specific integrated circuit (ASIC). ECU 32 may include a central processing unit (CPU) and an input/output (I/O) interface through which ECU 32 may receive a plurality of input signals including signals generated by device 26 (and particularly sensors 46) and patch electrodes 30 and generate a plurality of output signals including those used to control and/or provide data to device 26, display 34, and switch 50. In operation, ECU 32 generates signals to control switch 50 and thereby selectively energize patch electrodes 30. ECU 32 receives position signals from position sensors 46 on device 26 reflecting changes in voltage levels on sensors 46 and from the non-energized patch electrodes 30. ECU 32 uses the raw location data produced by sensors 46 and electrodes 30 and corrects the data to account for respiration and other artifacts. ECU 32 then generates display signals operable to generate an image or visualization on display 34.

Display 34 is provided to convey information to a physician to assist in diagnosis and treatment. Display 34 may comprise a conventional computer monitor or other display device. Display 34 presents a graphical user interface (GUI) to the physician. The GUI may include a variety of information including, for example, an image of the geometry of heart 24, EP data associated with heart 24, graphs illustrating voltage levels over time for various electrodes, and images of medical device 26 and related information indicative of the position of device 26 relative to heart 24 and coordinate system 48. In at least one embodiment, the system 28 may, for example, comprise the electroanatomical mapping and catheter navigation system and/or components thereof offered commercially under one or more of the trademarks "ENSITE", "ENSITE VELOCITY" and "ENSITE NAVX" by St. Jude Medical, Inc. Certain aspects of such a system are described, in part, in commonly assigned U.S. Pat. No. 7,263,397 titled "Method and Apparatus for Catheter Navigation and Location and Mapping in the Heart," the entire disclosure of which is incorporated herein by reference.

Figure 2:
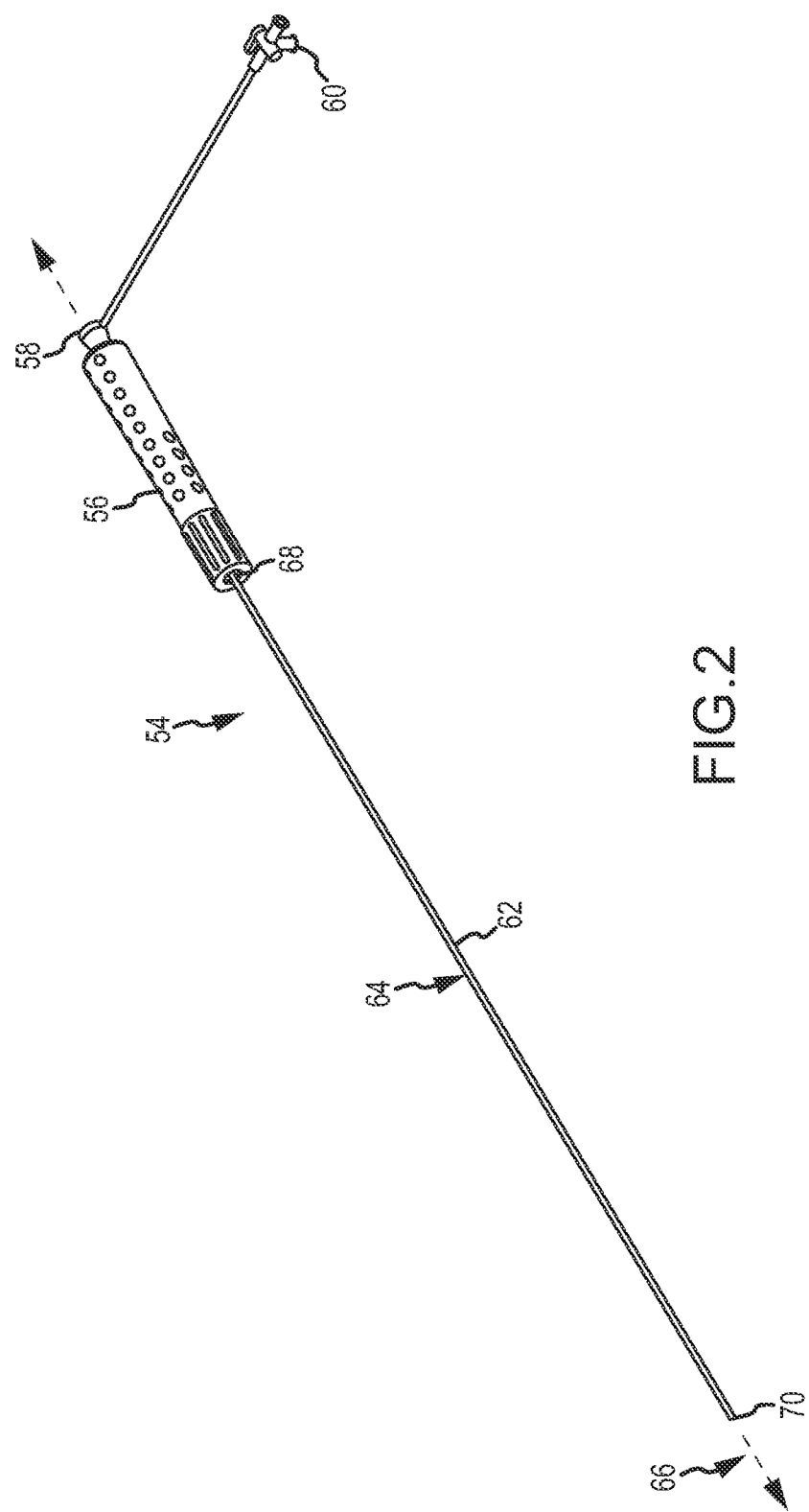
FIG. 2 is a perspective view of an introducer for a medical device.

In various embodiments and referring to FIG. 2, an introducer 54 may be used to insert the shaft 38 of device 26 into body 22. Introducer 54 may be provided to protect blood vessels and/or other anatomical structures as device 26 is guided and manipulated to a region of interest and to minimize loss of blood during exchange of guide wires and catheters. Introducer 54 may include a handle 56, a hub 58, a valve 60, and a sheath 62 in accordance with the present invention. Handle 56 is provided to guide or steer sheath 62 as sheath 62 is maneuvered within body 22. Handle 56 defines a lumen coaxially aligned with sheath 62 and through which shaft 38 of device 26 extends as well as additional lumens for passage of conductors and fluids to or from electrical and fluid connectors. Hub 58 may comprise a hemostasis valve that is provided to minimized fluid loss during the procedure and allow a medical device to pass into the introducer 54 and through sheath 62. Hub 58 is used to control movement of shaft 38 of device 26 within sheath 62 after insertion of shaft 38. Valve 60 is provided to introduce irrigant to and/or through sheath 62. Additional details regarding exemplary introducers, such as introducer 54 and the like, may be found in U.S. application Ser. No. 11/647,313 titled "Steerable Catheter Using Flag Pull Wires and Method of Making Same" (published as U.S. Publication No. 2007/0299424), hereby incorporated by reference as though fully set forth herein.

Figure 3:
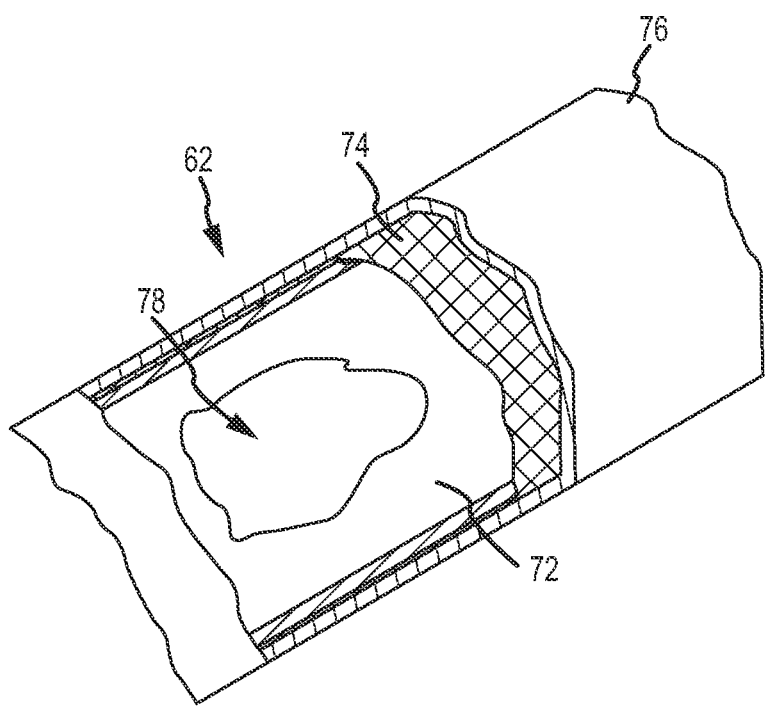
FIG. 3 is a perspective, cut-away view of a portion of an introducer sheath.

Sheath 62 is provided to guide device 26 (FIG. 1) to a target region while protecting vessel walls. Sheath 62 has a deformable, elongate, tubular body 64 disposed about a longitudinal axis 66 having a proximal end 68 near handle 56 and a distal end 70 defining a distal tip. Referring to FIG. 3, sheath 62 may include a tubular, polymeric inner liner 72, a braided wire layer 74 for torque transfer, and an outer polymeric jacket 76. Liner 72 is made from a polymeric material such as polyfluoroethylene (PTFE), polyether block amides, nylon or thermoplastic elastomers such as the elastomer sold under the registered trademark "PEBAX" by Arkema, Inc. Liner 72 defines a lumen 78 extending from proximal end 68 to distal end 70 of sheath 62 and configured to receive device 26 therein (and particularly shaft 38 of device 26). Braided wire layer 74 is configured to provide appropriate levels of pushability, torqueability, flexibility, and kink resistance to sheath 62. Layer 74 may be formed from stainless steel wire, preferably flat wire (wire having a cross-section that, when taken along the wire's longitudinal axis and measured along two orthogonal axes, is substantially rectangular) arranged in various braid patterns including one-over-one (involving at least two wires) or two-over-two (involving at least four wires) crossover patterns and having a pics (or "picks") per inch density between 5 and 100. The wire may be coated with a layer of an insulating material. The wire braid may be directly wound about liner 72 or placed on a core that is slid over liner 72. Jacket 76 is made from a polymeric material such as polyfluoroethylene (PTFE), polyether block amides, nylon or thermoplastic elastomers such as the elastomer sold under the registered trademark "PEBAX" by Arkema, Inc. and may be extruded over layer 74. Additional details regarding several exemplary sheath constructions may be found in commonly assigned U.S. Pat. No. 7,914,515 titled "Catheter and Introducer Catheter Having Torque Transfer Layer and Method of Manufacture," the entire disclosure of which is incorporated herein by reference.

Figure 4:
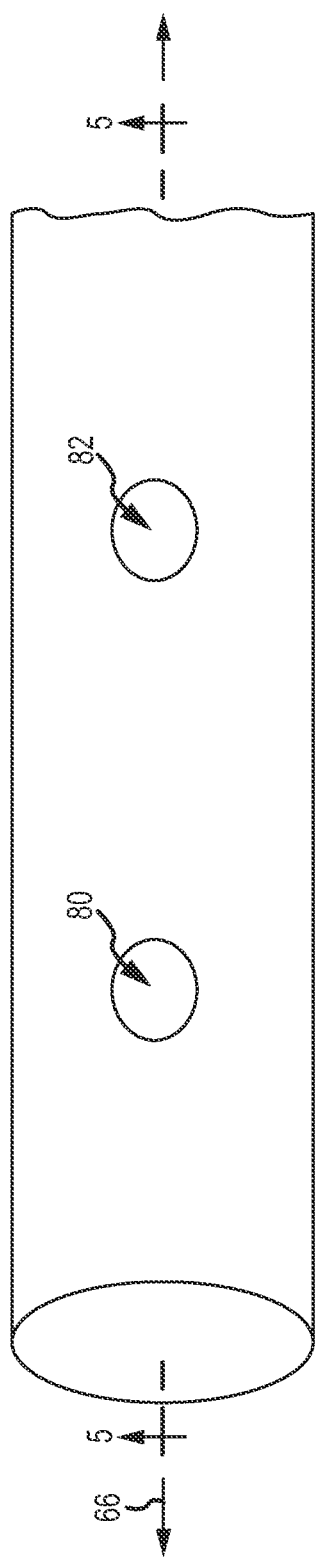
FIG. 4 is a plan view of an introducer sheath in accordance with one embodiment of the present invention.
Figure 4A:
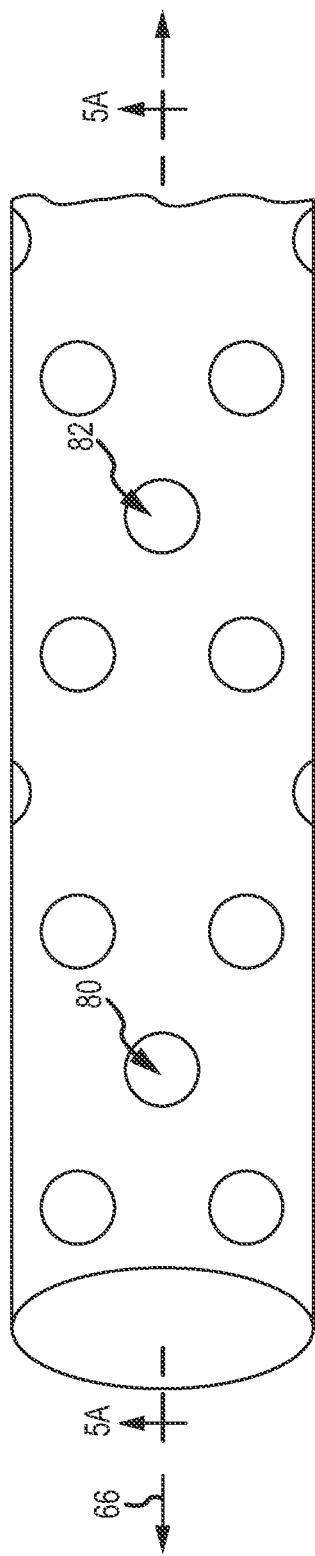
FIG. 4A is a plan view of an introducer sheath in accordance with another embodiment of the present invention.
Figure 4B:
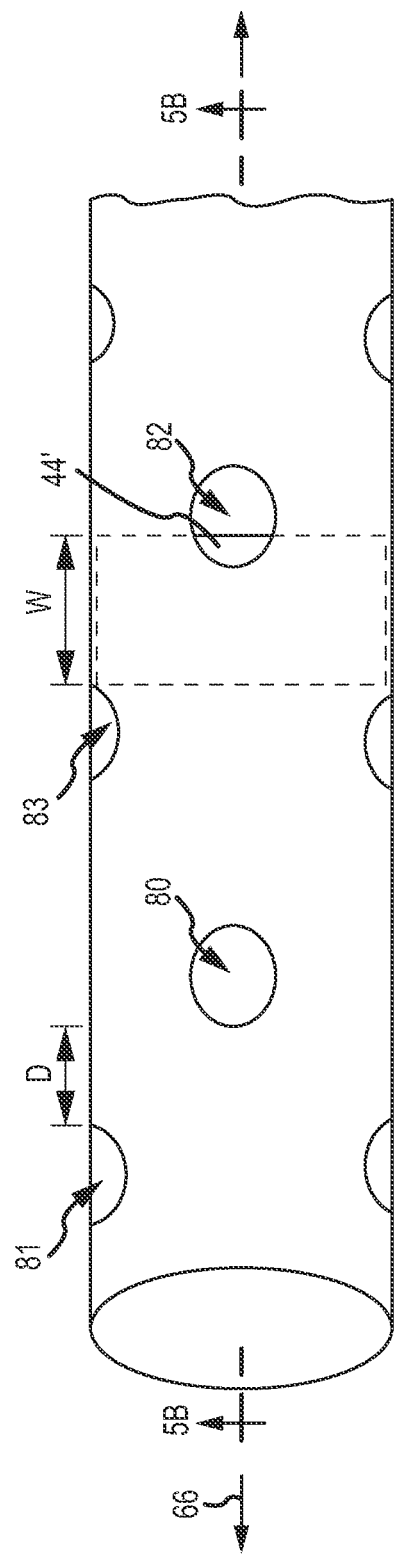
FIG. 4B is a plan view of an introducer sheath in accordance with another embodiment of the present invention.

Referring now to FIGS. 4-5, one embodiment of an introducer sheath 62 in accordance with the present invention is illustrated. In particular, sheath 62 includes one or more apertures 80, 82 extending radially from a radially outer surface 84 of sheath 62 to lumen 78. Apertures 80, 82 establish a passage between lumen 78 and the space outside of sheath 62 for transmission of ions thereby electrically coupling the space defined by lumen 78 with the space outside of sheath 62 such that an electric field within lumen 78 may be similar to an electric field outside of sheath 62. Apertures 80, 82 allow electric current generated by electrical activity in body tissues or from external sources such as patch electrodes 30 to pass radially between surface 84 and lumen 78 to electrodes 44, 46 on medical device 26. Apertures 80, 82 are located primarily at the distal end of sheath 62 which will be disposed close to the anatomical region of interest and where positional information regarding device 26 is most important. In the illustrated embodiment, there are two circular apertures 80, 82 disposed in a line extending parallel to the longitudinal axis 66 of sheath 62. It should be understood, however, that various modifications could be made to the arrangement of apertures 80, 82. For example, the number of apertures 80, 82 could be varied substantially from as few as one aperture to many more than two. The shape of apertures 80, 82 could be rectilinear or formed from a variety of other shapes and patterns. As opposed to being arranged in a straight line parallel to the longitudinal axis 66 of sheath 62, apertures 80, 82 could be arranged in various paths that are not parallel and/or not straight. For example, and as seen in FIGS. 4A and 5A, a spiral pattern and/or braid-like pattern may be used so as to not substantially compromise strength in the wall of sheath 62. As seen in FIGS. 4B and 5B, multiple rows or paths of apertures could also be employed including arrangements such that apertures 80 and 82 are diametrically opposite apertures 80' and 82' or cross one another similar to a braid. Apertures 80, 82 could also be arranged at predetermined equal or unequal angular or linear spacings around the circumference of sheath 62. Apertures 80, 82 may also be of different sizes and, in accordance with one embodiment of the invention, aperture 82 may be larger than aperture 80 and may be located nearer to distal end 70 of sheath 62 than aperture 80. In one constructed embodiment, a sheath was made having three rows of circular apertures having a size of about 0.054 inches and a spacing of about 5 millimeters between apertures with a total of approximately 80 apertures. In another constructed embodiment, a sheath was made having six rows of circular apertures having a size of about 0.023 inches and a spacing of about 2.5 millimeters between apertures with a total of approximately 250 apertures. In these and other embodiments and referring again to FIG. 4B, apertures, such as apertures 80 and 81, representing apertures from different rows or different circumferentially located sets of apertures, may be longitudinally spaced apart from each other such that when an electrode, such as electrode 44', of a medical device (remainder of device not drawn for clarity) is positioned within a distal section of the body 64 of sheath 62 as shown and moved relative to the sheath's body 64, at least a portion of the electrode 44' is continuously adjacent at least one aperture. In other words, the distance "D" between apertures 80 and 81 may be such that an electrode of width "W" (typically about 1 millimeter) may consistently be next to at least one aperture, such as aperture 82 as shown. If the electrode 44' were moved to the left in the page of FIG. 4B, then electrode 44' may no longer be adjacent aperture 82, but it may then have at least a portion adjacent aperture 83. Referring to FIG. 6, each aperture, such as aperture 80 as illustrated may extend through a space 88 formed between the pics 86 in braided wire layer 74 of sheath 62 (i.e. between locations at which wires in the braid cross). In accordance with another embodiment of the invention, apertures 80, 82 may also communicate with a lumen (not shown) formed in one of the layers of sheath 62 and extending from a proximal end of sheath 62 such that an irrigating fluid (e.g., saline) can be used to flush apertures 80, 82 and prevent ingress of blood or other body fluids. In at least one embodiment, irrigant may be delivered to apertures 80, 82 via lumen 78.

Figure 8:
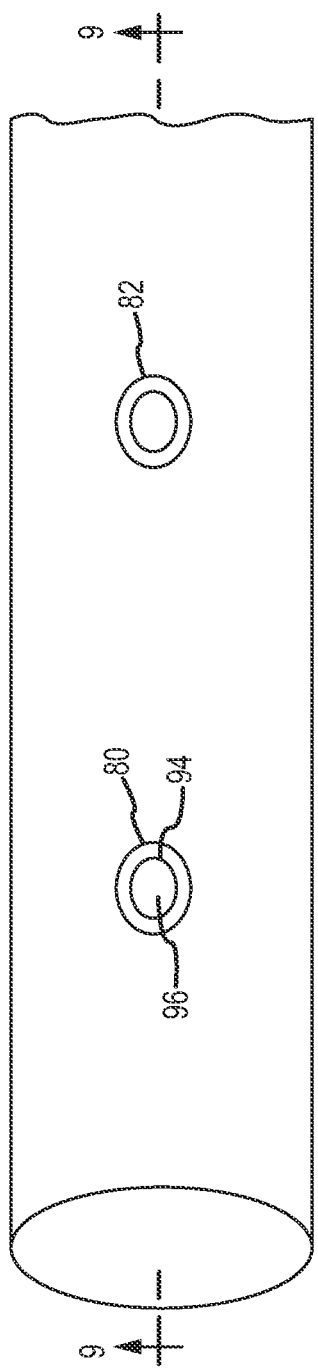
FIG. 8 is a plan view of an introducer sheath in accordance with another embodiment of the present invention.
Figure 9:
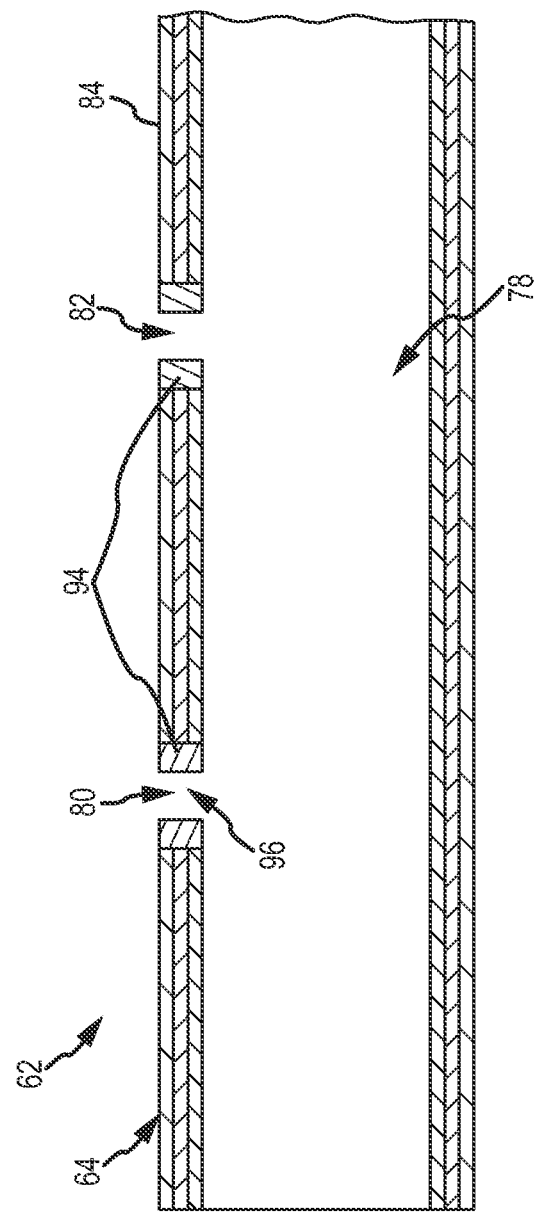
FIG. 9 s a cross-sectional view of the introducer sheath of FIG. 8 taken along lines 9-9.

As noted above, apertures 80, 82 in body 64 of sheath 62 may be open from radially outer surface 84 to lumen 78. Referring now to FIGS. 7-9, in an alternative embodiment of the invention, apertures 80, 82 may be filled in whole or in part with an electrically conductive material or member that allows passage of the electric currents from a space outside the sheath, that is beyond radially outer surface 84 to inside the sheath, that is within lumen 78. The members may incorporate features to mechanically fix the members to the wall of the apertures 80, 82. Referring to FIG. 7, in accordance with one embodiment of the invention, a hydrogel 92 is disposed within one or both apertures 80, 82. Alternatively, a cellulosic casing material may be used. Referring to FIGS. 8-9, in another alternative embodiment, tungsten members 94 may be disposed within apertures 80, 82. Members 94 may be solid or, as shown in FIGS. 8-9, may define radially extending bores 96 configured to allow passage of ions between surface 84 and lumen 78. It should be understood that tungsten is an exemplary material and that members 94 may be formed from a variety of electrically conductive materials including other metals and metal alloys such as gold or steel. In addition to the ability of obtain position data, if apertures 80, 82 are spaced closely enough (e.g., 3-10 millimeters), electrogram signals may be sampled by electrodes 44 on device 26 and EP data may be generated by ECU 32 through conventional interpolation methods. In accordance with another aspect of the invention, apertures such as apertures 80, 82 and members 94 disposed within those apertures may be spaced at regular or equal distances or in some other predetermined pattern such that members 94 may be used as markers in fluoroscopic or other imaging methodologies to provide position information including, for example, information regarding the position of sheath 62 relative to an anatomical region of interest and information regarding the position of device 26 (FIG. 1) within sheath 62.

Referring now to FIG. 10, in accordance with another alternative embodiment of the invention, the use of conductors within or on the inner or outer surface of body 64 of sheath 62 may be used to facilitate transmission of the electric currents from outside sheath 62 to locations within lumen 78 and reduce the number of required apertures formed in body 64. In particular, one or more strips 98 of electrically conductive material, such as a metal or an extruded conductive polymer, may be disposed on a surface of body 64 such as a radially inner surface 85. Strips 98 may have a higher electrical conductivity than other portions of body 64 adjacent to strips 98 and strips 98 may extend between apertures 80, 82 as shown or from an aperture 80 or 82 to a predetermined point on the inner or outer surface of body 64. The configuration (e.g., size) and material for strips 98 may be selected such that the impedance of the material avoids or resists shorting the navigation and electrophysiology fields (e.g., a material with an impedance of about 200-800 ohms) and the conductivity of the material is substantially similar to that of blood. Strips 98 may find particular use where the amount of saline or heparinized blood within lumen 78 is relatively low due to displacement by device 26 (FIG. 1) positioned at least partially within lumen 78. As an alternative to strips 98, one or more saline channels may extend through body 64 to transport current between apertures 80, 82 or from an aperture 80 or 82 to a predetermined point on the inner or outer surface of body 64.

In at least one embodiment and referring to FIG. 11, the walls of apertures 80, 82 and/or the surfaces of liner 72 or jacket 76 proximate apertures 80, 82 may be coated with a hydrophilic substance 100 and, in particular, a heparinized hydrophilic substance. Such a substance may help reduce the risk of thrombus formation during use in a patient. Alternatively (or additionally), and with reference to FIGS. 12A-B, a sleeve 102 may be disposed within lumen 78 and moved longitudinally relative to body 64 to provide selective communication between apertures 80, 82 and lumen 78. Sleeve 102 has an outer diameter that is about the same or slightly smaller than as an inner diameter of body 64. Sleeve 102 may define one or more radially extending openings 104, 106 that can be selectively moved from a first position (shown in FIG. 12A) where openings 104, 106 are not radially aligned with apertures 80, 82 to a second position (shown in FIG. 12B) where openings 104, 106 are brought into radial alignment with apertures 80, 82 whenever it is desirable for electric current to pass through body 64 and into lumen 78 (e.g., for position sensing or electrogram readings). In this manner, communication with lumen 78 is restricted to periods of required measurements and the risk of thrombus formation may likewise be reduced. Sleeve 102 may be moved within lumen 78 using a pull wire or other conventional means and actuated at handle 56 (FIG. 2).

Referring now to FIGS. 13A-B, in accordance with another aspect of the invention, a sleeve 108 may also be used within a sheath 110 to control the transmission of electric current through apertures 112, 114, 116 in sheath 110 and the type of measurements made by a medical device 26 within sheath 110. Sleeve 108 may define one or more radially extending openings 118, 120, 122. The relative positioning and spacing among openings 118, 120, 122 may be varied, however, relative to the positioning and spacing of apertures 112, 114, 116 in sheath 110. In the illustrated embodiment, for example, when sleeve 108 is in a first position relative to sheath 110 (shown in FIG. 13A), openings 120, 122 are aligned with apertures 114, 116 such that the apertures 114, 116 in communication with lumen 78 are relatively closely spaced. When sleeve 108 is in a second position relative to sheath 110 (shown in FIG. 13B), openings 118, 120 are aligned with apertures 112, 116 such that the apertures 112, 116 in communication with lumen 78 are relatively distantly spaced. In this manner, different electrogram measurements can be obtained by varying the entry point of the electric currents into sheath 110. It should be understood that apertures 112, 114, 116 in sheath 110 and openings 118, 120, 122 in sleeve 108 could be arranged in a variety of ways to achieve similar results. For example, although the illustrated embodiment shows substantially even spacing between apertures 112, 114, 116 in sheath 110 and uneven spacing between openings 118, 120, 122 in sleeve 108, it should be understood that this arrangement could be reversed with similar effect.

Referring now to FIG. 14, another embodiment of an introducer sheath 124 in accordance with the present invention is illustrated. Sheath 124 is substantially similar to sheath 62 described hereinabove. Unlike sheath 62, however, sheath 124 does not include apertures 80, 82. Rather, sheath 124 includes a body 126 having one or more longitudinal sections 128, 130 made from an electrically conductive material. The electrical conductivity of sections 128, 130 is higher than the electrical conductivity of adjacent longitudinal sections 132, 134, 136 of body 126 and permits the passage of electric current from a radially outer surface 138 of body 126 to a lumen 140 in which a medical device 26 is disposed. The electrical conductivity of sections 128, 130 may be substantially equal to an electrical conductivity of blood. Sections 128, 130 may be made from an electrically conductive polymer such as a tungsten doped thermoplastic polymer (the polymer may, for example, comprise the polymer sold under the registered trademark "PEBAX" by Arkema, Inc.) or from metal. In the case where sections 128, 130 are made from a polymer, sections 128, 130 may be joined to adjacent sections 132, 134, 136 made from the same or a similar polymer (but without, or with less of, the tungsten or other element providing the increased conductivity to sections 128, 130) by melting (reflowing) the sections together around a mandrel.

Figure 15:
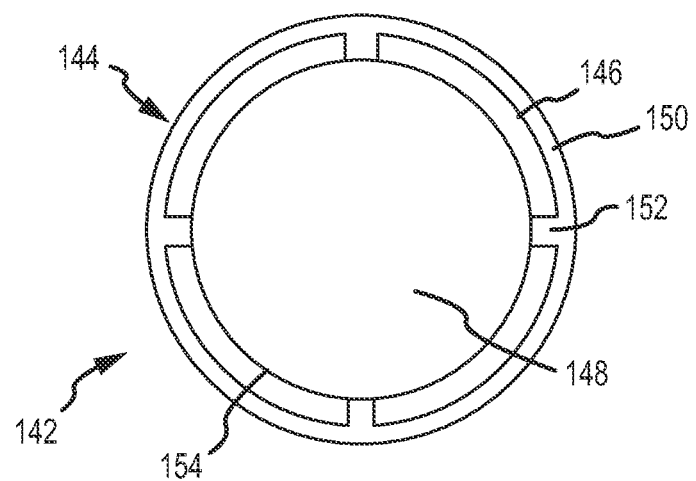
FIG. 15 is a cross-sectional view of an introducer sheath in accordance with another embodiment of the present invention.

Referring now to FIG. 15, another embodiment of an introducer sheath 142 in accordance with the present invention is illustrated. Sheath 142 is also similar to sheath 124 described hereinabove in that sheath 142 includes one or more longitudinal sections 144 having an electrical conductivity that is higher than the electrical conductivity of adjacent longitudinal sections of the body of the sheath 142 to permit passage of electric current from a radially outer surface 146 of the body to a lumen 148 in which a medical device 26 is disposed. The electrical conductivity of section 144 is provided by a ring 150 of conductive material on surface 146 of sheath 142. Ring 150 may be substantially similar to ring electrodes found on device 26, for example, and may be made from conventional conductive metals such as platinum, iridium, gold, and silver and metal alloys including stainless steel and Nitinol. Ring 150 includes one or more radially inwardly extending portions 152 that extend to radially inner surface 154 of sheath 142 where they are exposed to lumen 148 and/or electrodes on device 26.

Figure 16:
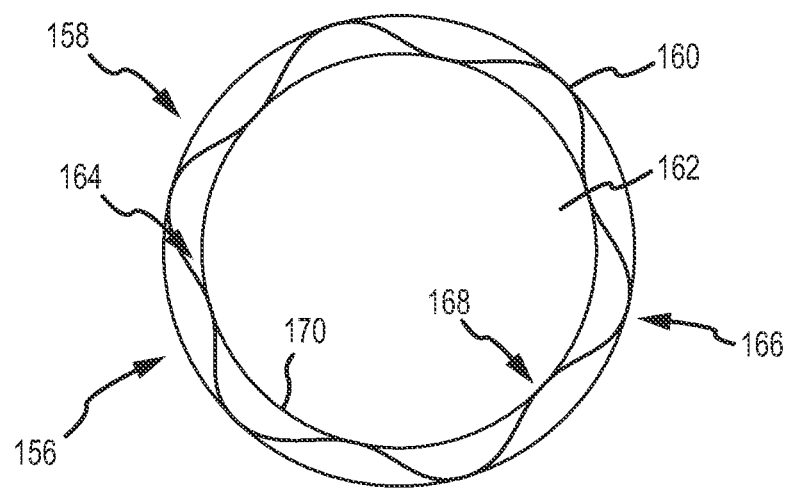
FIG. 16 is a cross-sectional view of an introducer sheath in accordance with another embodiment of the present invention.

Referring now to FIG. 16, another embodiment of an introducer sheath 156 in accordance with the present invention is illustrated. Sheath 156 is similar to sheath 124 described hereinabove in that sheath 156 includes one or more longitudinal sections 158 having an electrical conductivity that is higher than the electrical conductivity of adjacent longitudinal sections of the body of the sheath 156 to permit passage of electric current from a radially outer surface 160 of the body to a lumen 162 in which a medical device 26 may be disposed. The electrical conductivity of section 158 is provided by a conductive insert 164 having one or more portions 166 exposed at surface 160 of section 158 and one or more portions 168 exposed at a radially inner surface 170 of section 158. As shown in the illustrated embodiment, insert 164 may be a corrugated ring. It should be understood, however, that the shape of insert 164 may vary.

Figure 17:
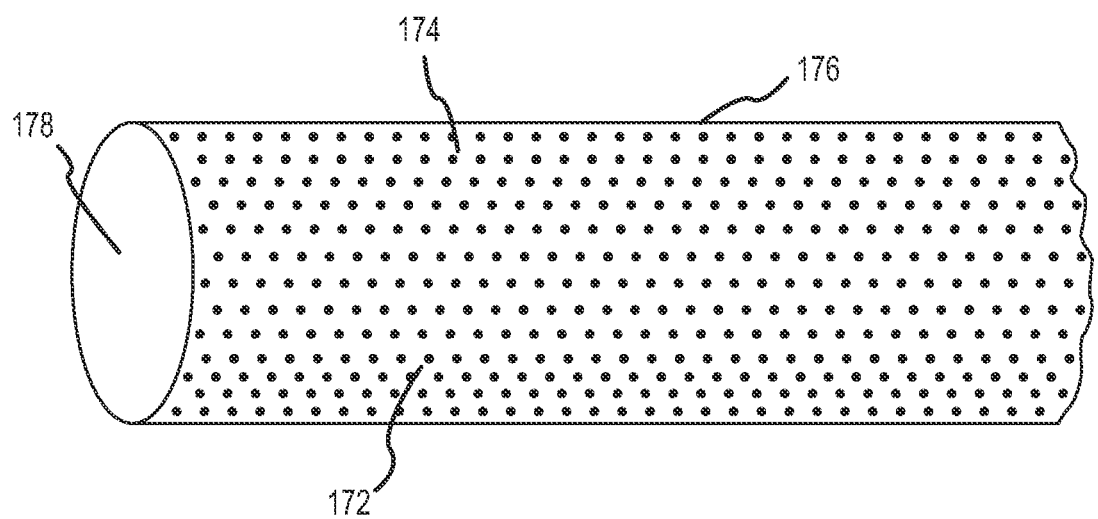
FIG. 17 is a plan view of an introducer sheath in accordance with another embodiment of the present invention.

Referring now to FIG. 17, another embodiment of an introducer sheath 172 in accordance with the present invention is illustrated. The body of sheath 172 is formed from a polymeric membrane having a specific permeability to a liquid carrying ions from the electric current. In particular, the body may be made from a polymeric material such as polyfluoroethylene (PTFE), polyether block amides, nylon or thermoplastic elastomers such as the elastomer sold under the registered trademark "PEBAX" by Arkema, Inc. A plurality of microscopic pores 174 may be formed in the body by incorporating fibers extending from a radially outer surface 176 of the body to the lumen 178 defined by the body during formation of the body and then dissolving the fibers or chemically etching away the fibers. Pores 174 are sized (e.g., less than two micrometers) to permit passage of ions from surface 176 to lumen 178 while preventing passage of blood platelets, thereby allowing electrical current to pass into the sheath, while limiting or preventing thrombus formation.

An introducer sheath in accordance with the present invention is advantageous relative to conventional introducer sheaths because the inventive sheath permits the passage of external electric currents generated by body electrical activity or sources external to the body to reach the medical device contained in the sheath. As a result, the device can monitor electrical activity of surrounding tissues while in the sheath. The device can also be tracked and guided using medical positioning systems employing electric fields.

Although several embodiments of this invention have been described above with a certain degree of particularity, those skilled in the art could make numerous alterations to the disclosed embodiments without departing from the scope of this invention. All directional references (e.g., proximal, distal, upper, lower, upward, downward, left, right, leftward, rightward, top, bottom, above, below, vertical, horizontal, clockwise and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not as limiting. Changes in detail or structure may be made without departing from the invention as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. An introducer sheath for a medical device, comprising:
   a deformable, elongate body disposed about a longitudinal axis, said body having proximal and distal ends and defining a lumen extending between said proximal and distal ends and configured to allow passage of the medical device therethrough;
   a first aperture extending from a radially outer surface of said body to said lumen; and
   a sleeve disposed within said lumen, said sleeve defining a first radially extending opening and being axially movable within said lumen to selectively align said first aperture in said body and said opening in said sleeve,
   wherein said body is configured to allow an electric current to pass radially between a space outside said body and said lumen,
   wherein said distal end of said body defines a tip that is configured to allow the medical device to exit the sheath, and
   wherein said lumen is sized and configured to allow fluid to flow around said medical device from said proximal end to said tip.

2. The introducer sheath of claim 1 wherein said first aperture extends through a space formed between a plurality of pics in a braided wire layer of said body.

3. The introducer sheath of claim 1 wherein a radially extending wall defining said first aperture is coated with a hydrophilic substance.

4. The introducer sheath of claim 1 wherein said radially outer surface of said body adjacent said first aperture is coated with a hydrophilic substance.

5. The introducer sheath of claim 1 wherein said first aperture includes a member made from an electrically conductive material disposed therein.

6. The introducer sheath of claim 5 wherein said member defines a radially extending bore extending therethrough.

7. The introducer sheath of claim 1 wherein a second aperture extends from said radially outer surface of said body to said lumen.

8. The introducer sheath of claim 7 wherein said first aperture is nearer said distal end of said body than said second aperture.

9. The introducer sheath of claim 8 wherein said first aperture is larger than said second aperture.

10. The introducer sheath of claim 7 wherein said body includes a strip of material extending between said first and second apertures having a higher electrical conductivity than portions of said body adjacent to said strip.

11. The introducer sheath of claim 7 wherein said sleeve further defines a second radially extending opening and said sleeve axially movable within said lumen to align said first and second openings with said first and second apertures when said sleeve is in a first position and to align said first and second openings with one of said first or second apertures and a third aperture, said third aperture extending from said radially outer surface of said body to said lumen, when said sleeve is in a second position.

12. The introducer sheath of claim 7 wherein said sleeve further defines second and third radially extending openings and said sleeve axially movable within said lumen to align said first and second openings with said first and second apertures when said sleeve is in a first position and to align one of said first or second openings and said third opening with one of said first or second apertures and a third aperture, said third aperture extending from said radially outer surface of said body to said lumen, when said sleeve is in a second position.

13. The introducer sheath of claim 12 wherein a distance between said first and second apertures differs from a distance between said one aperture and said third aperture.

14. The introducer sheath of claim 1 wherein a first longitudinal section of said body is made from an electrically conductive material and second and third longitudinal sections adjacent to opposite longitudinal ends of said first longitudinal section are made from a material having a lower conductivity than said electrically conductive material.

15. The introducer sheath of claim 14 wherein said electrically conductive material has an electrical conductivity configured to be substantially equal to an electrical conductivity of blood.

16. The introducer sheath of claim 1 wherein said body is formed from a polymeric membrane having a specific permeability to a liquid carrying said electric current.

17. The introducer sheath of claim 1 wherein said body comprises a distal section and a plurality of apertures extend from a radially outer surface of said body to said lumen, said plurality of apertures longitudinally spaced apart from each other such that when an electrode of the medical device is positioned within said distal section and moved relative to said body, at least a portion of the electrode is continuously adjacent at least one aperture of said plurality of apertures.

18. An introducer sheath for a medical device, comprising:
   an elongate body disposed about a longitudinal axis, said body having proximal and distal ends and defining a lumen extending between said proximal and distal ends and configured to allow passage of the medical device therethrough; and
   a first aperture and a second aperture extending from a radially outer surface of said body to said lumen; and,
   wherein said distal end of said body is configured to allow the medical device to pass through the body to an exterior portion of the body, wherein said lumen is sized and configured to allow fluid to flow around said medical device from said proximal end to said distal end, and wherein a strip of material is disposed on an inner surface of said body and said strip of material extends between said first and second apertures and has a higher electrical conductivity than portions of said body adjacent to said strip.

19. An introducer sheath for a medical device, comprising:

a deformable, elongate body disposed about a longitudinal axis, said body having proximal and distal ends and defining a lumen extending between said proximal and distal ends and configured to allow passage of the medical device therethrough;

a first aperture extending from a radially outer surface of said body to said lumen; and a second aperture extending from said radially outer surface of said body to said lumen, wherein said distal end of said body defines a tip that is configured to allow the medical device to exit the sheath, wherein said lumen is sized and configured to allow fluid to flow around said medical device from said proximal end to said tip, and wherein a strip of material is disposed on an inner surface of said body and said strip of material extends between said first and second apertures and has a higher electrical conductivity than portions of said body adjacent to said strip.

\* \* \* \* \*